(12) United States Patent
Haefele et al.

(10) Patent No.: US 6,331,156 B1
(45) Date of Patent: Dec. 18, 2001

(54) ELECTRONIC ENDOSCOPE

(75) Inventors: Ulrich Haefele, Oberderdingen; Michael Voegele, Kaempfelbach, both of (DE)

(73) Assignee: Richard Wolf GmbH, Knittingen (DE)

( * ) Notice: Subject to any disclaimer, the term of this patent is extended or adjusted under 35 U.S.C. 154(b) by 0 days.

(21) Appl. No.: 09/589,846

(22) Filed: Jun. 8, 2000

(30) Foreign Application Priority Data

Jun. 21, 1999 (DE) .......................................... 299 10 795 U

(51) Int. Cl.$^7$ .......................................................... A61B 1/07
(52) U.S. Cl. ............................................ 600/179; 362/574
(58) Field of Search ..................................... 600/178, 179, 600/182; 362/555, 574; 348/68

(56) References Cited

U.S. PATENT DOCUMENTS 3,042,022 * 7/1962 Sheldon .............................. 600/179

FOREIGN PATENT DOCUMENTS 296 13 103 U 1   11/1997 (DE).
298 12 048 U 1   12/1998 (DE).

* cited by examiner

*Primary Examiner*—John Mulcahy
(74) *Attorney, Agent, or Firm*—Akin, Gump, Strauss, Hauer & Feld, L.L.P.

(57) ABSTRACT

An electronic endoscope with a picture sensor located at its distal end and with several illumination units (LEDs) integrated in the endoscope, for producing illumination light irradiated at the distal endoscope end. The illumination units are arranged as a linear and axial array of LEDs in a space, of an enveloping tube, connecting proximally to the picture sensor. To the LEDs there are allocated fiber-optics into which the light irradiated by the LEDs may be coupled. The fiber-optics run up to the distal endoscope end and here are grouped together to a bundle.

17 Claims, 5 Drawing Sheets

ELECTRONIC ENDOSCOPE

BACKGROUND OF THE INVENTION

The invention relates to an electronic endoscope with a picture sensor located at its distal end and with several illumination units integrated in the endoscope, for producing illumination light irradiated at the distal endoscope end.

With such an electronic endoscope (DE 296 13 103 U1, DE 298 12 048 U1) e.g. in cancer diagnosis, photosensitive substances which are accumulated in the body may be stimulated by way of stimulation light for the fluorescence irradiation. The fluorescence stimulation may be carried out with LEDs producing single-colored light, e.g. blue, green or red light, illumination units in combination with a black and white CCD chip as a picture sensor with dichroitic filters. With the known electronic endoscope known from the above publication the LEDs serving the illumination are arranged at the distal endoscope end. On account of the constructional size of the LEDs, the outer diameter of the endoscope increases disadvantageously.

Generally electronic endoscopes beyond the early primary field of application of diagnosis are also applied in surgery, in particular minimalinvasive surgery, with which the operation field may be shown on a monitor for the whole operating team.

With a typical endoscope used in minimal-invasive surgery at the proximal end thereof via an objective a camera head is adapted. This is connected to a camera controller which converts the signals coming from the camera head into a picture which can be displayed on a monitor. The illumination light is supplied from the outside and moves from a light source via a fiber-optic to a light exit at the distal end of the endoscope. This arrangement however has the disadvantage that the camera head must be adapted onto the proximal end of the endoscope via an objective. This has considerable ergonomic disadvantages since the dimensions of the head and objective only permit a miniaturization to a limited extent.

Furthermore the picture definition with each change in endoscope must be manually adapted at the objective. By way of the numerous air-glass transitions in the endoscope, in the objective and in the camera head, with the picture brightness there occurs losses. With the use of endoscopes of various diameters the picture size must be compensated at the monitor by the use of objectives of differing focal distances, or a zoom objective must be used. This however compared to an objective with a fixed focal distance has larger dimensions and a higher weight which in turn has a disadvantageous effect on the ergonomics.

The electronic endoscopes common in the meantime with the advancing development of semiconductor technology are distinguished in that the picture sensor is no longer arranged proximally but distally in the endoscope. This has the result that all manual corrections with respect to the picture definition and focal length adaptation are done away with and occurring losses of the picture brightness are reduced on account of the low number of optical components. The handling is improved by the small dimensions of a proximally arranged plug, and the objective for camera adaptation necessary with the previously described endoscope may be done away with.

With a known embodiment form of such an electronic endoscope illumination light from an external light source via a fiber-optic bundle is coupled into the endoscope. At the proximal end of the electronic endoscope there is mounted a connection plug which permits a separation of the electronic endoscope from the connection cable leading to the camera controller. This has the advantage that for several electronic endoscopes only one connection cable type is required, which increases the economic efficiency of the system.

According to experience this connection cable from the electronic endoscope to the camera controller, on account of its mechanical loading, causes the greatest breakdown rate in the whole system. For this reason also for this, the separability of the connection cable from the electronic cable has shown to be advantageous, since by way of the exchangeability of the connection cable by the personnel on location, the running costs are reduced and the endoscope with a failure or breakage of the cable does not have to be sent back to the manufacturer for repair.

A disadvantage of such an endoscope is however the fact that the fiber-optic connection is no longer rotatable to the position of the picture sensor. In comparison to this with the firstly described endoscope with a proximally attached video camera, by way of rotating the camera head or the objective, the position of the picture on the monitor may be corrected such that the picture is no longer displayed on the monitor head first. Thus the fiber-optic connection with this endoscope by rotation of this endoscope may be brought into a favorable position without the picture on the monitor being shown in the wrong position.

With an endoscope system a rotation of the electronic endoscope compellingly has the consequence of a rotation of the picture on the monitor. This means that the endoscope must be located in a certain position in order to represent the picture in the correct position on the monitor. Under certain conditions this fact may lead to problems, since the endoscope, according to application, is not always located in the same position and on account of the forces which are exerted by the fiber-optic onto the endoscope, may be undesirably rotated which simultaneously means a rotation of the picture on the monitor. This may lead to the fact that the surgeon loses the orientation, since the operating region is no longer shown on the monitor in the correct position.

With a further known endoscope the actual electronic endoscope including the fiber-optic and the connection cable form one unit. The fiber-optic integrated in this unit, from the distal end of the endoscope up to the other end, of the fiber-optic, which is located in the light source, is designed without interruption as one piece. This has the advantage that by way of this no additional light losses arise at a coupling location between the fiber-optic and endoscope and thus a maximum of illumination light is guided further to the distal end. This embodiment form although improving the handling with regard the rotating of the endoscope, is however not yet optimal since the integrated fiber-optic cable and the camera cable are relatively heavy and thus increase the total weight of the system.

Furthermore with this known embodiment form of an electronic endoscope cable breakage is of a great disadvantage. If specifically the fiber-optic cable or the camera cable is defective, a repair at the place of the manufacturer is necessary, since on location the cable may not be professionally repaired or replaced. In the factory of the manufacturer the endoscope unit under certain circumstances must be completely disassembled for the repair. By way of this the running costs are increased and the interruption times are lengthened.

BRIEF SUMMARY OF THE INVENTION

The object of the invention lies in the provision of an electronic endoscope, with which the handling and ergonomics are improved with a simultaneous optimal economic efficiency and with which, in spite of integrated illumination means, the outer diameter of the endoscope shank may be kept small.

With an electronic endoscope of the known type, according to the invention this object is achieved in that the illumination units are arranged as a linear and axial array of LEDs in a space, of an enveloping tube of the endoscope, which connects proximally to the distal picture sensor, that to the LEDs there are allocated fiber-optics into which the light irradiated by the LEDs may be coupled, and that the fiber-optics run up to the distal endoscope end and here are grouped together to a bundle.

Thus with such an endoscope one may do away with an external light source and a fiber-optic cable coupling this light source to the endoscope, so that between the endoscope and a camera controller only a connection cable leading electrical signals is required, this advantageously being able to be coupled to a plug at the proximal end of the endoscope. The difficulty which sets in on rotation of the endoscope on account of the forces which act via the fiber-optic on the endoscope are thus ruled out. In spite of this there completely remains the advantage of the releasable connection between the proximal end of the endoscope and the connection cable. This has the effect of an improved economic efficiency and ergonomics. Since the outer fiber-optic is done away with, the reliability of the whole system is increased. With one embodiment form the linearly and axially arranged LEDs may be set exclusively for emitting white light. With an alternative embodiment form the LEDs may be set up for emitting white and monochromatic light.

In order to produce various spectral regions of illumination light, there may be provided means for changing over the spectrum of the light irradiated from the fiber-optic bundle at the distal end.

Advantageously these change-over means change over the LEDs themselves. The linearly and axially arranged array of LEDs may contain a first group of white LEDs or LEDs producing white light and a second group of LEDs irradiating monochromatic light. With this arrangement the fiber-optic bundle at the distal end may simultaneously emit white and monochromatic light for the spectral correction of the white light.

The mentioned change-over means may with this be provided for the change-over of the color temperature of the light irradiated at the distal end of the electronic endoscope. The change-over means may also change over between a first LED group comprising n white LEDs and m monochromatic LEDs and a second group comprising i white LEDs and k monochromatic LEDs.

With a preferred embodiment form the array of all LEDs is arranged on a common circuit board within the space formed in the enveloping tube such that the light irradiation of all LEDs is effected radially in one direction.

With this the fiber-optics from each LED are led radially outwards and then within the enveloping tube in the axial direction to the distal end or alternatively only from every second LED firstly radially outwards and then within the enveloping tube in the axial direction to the distal end. With the alternative embodiment the array of LEDs may be set up such that the even-numbered LEDs emit white light and the odd-numbered LEDs monochromatic light. With this a change-over means for the axial displacement of the common circuit board accommodating the array of LEDs may be set up such that into the fiber-optic, in a first position of the circuit board, there is coupled only white light from the even-numbered LEDs and in a second position of the circuit board there is coupled only monochromatic light from the odd-numbered LEDs.

BRIEF DESCRIPTION OF THE DRAWINGS

The invention is hereinafter described by way of embodiment examples schematically represented in the drawings. There are shown.

DETAILED DESCRIPTION OF THE INVENTION

Figure 1:
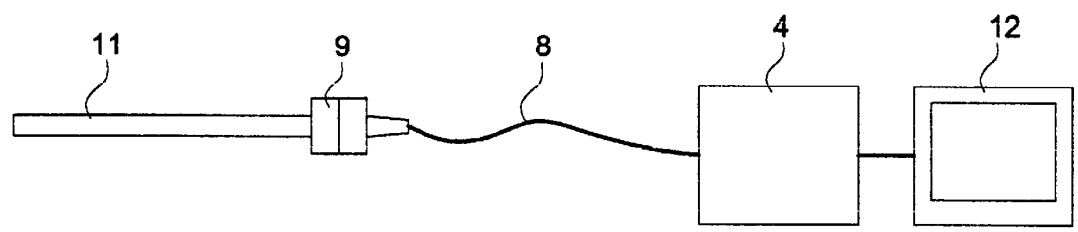
FIG. 1 the system structure of an electronic endoscope formed according to the invention with a connected camera controller and monitor, FIG. 2 in the form of a longitudinal section, the inner construction of an embodiment example of an endoscope according to the invention, FIGS. 3a–3d in each case differing embodiment forms of a LED illumination unit used with the endoscope according to the invention, FIGS. 4a–4b a further embodiment form of an LED illumination unit used with the endoscope, in each case in a plane view from above and in an elevation, FIGS. 5a–5b in each case in a partly sectioned plan view and in cross section according to section line A—A an embodiment form, optimized from the point of view of manufacturing technology, of an electronic endoscope with the illumination unit shown in the FIGS. 3c and 3d and FIGS. 6a–6b in the form of a partly sectioned plan view an advantageous further formation of the embodiment form shown in the FIGS. 5a and 5b, of an endoscope according to the invention.

FIG. 1 shows in function blocks an electronic endoscope system according to the invention as a whole. The endoscope 11 contains the illumination units whose design and structure is discussed further below, and comprises at its proximal end a plug connection 9 to which there may be stuck on a connection cable 8 to a camera controller 4. To the camera controller 4 there is connected a monitor 12. The voltage supply for the illumination units integrated in the endoscope 11 may advantageously be tapped from the operating voltage of the picture sensor provided at the distal end of the electronic endoscope 11. In this manner the connection cable 8 between the plug connection 9 and the camera controller 4 must only lead the electronic camera signals and feed voltages between the camera controller 4 and the electronic endoscope 11.

The difficulty that the endoscope is rotated by a separately supplied fiber-optic cable is avoided with the system shown in FIG. 1. However the advantage of the releasable connection between the plug connection 9 and the connection cable 8 remains in its entirety. This has an advantageous effect on the economic efficiency and the ergonomics. Since the fiber-optic outside the endoscope is done away with, the reliability of the whole system is high. Furthermore the LEDs used for the illumination units in the electronic endoscope extend the life duration of the electronic endoscope since they themselves have a long life duration.

Figure 2:
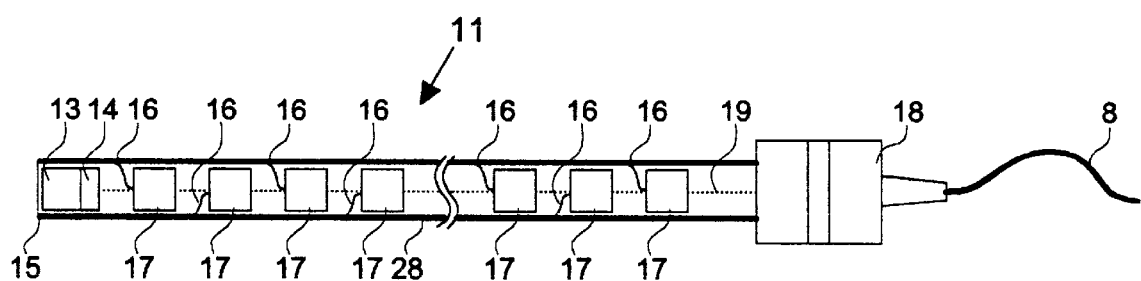

FIG. 2 shows the principle construction of an endoscope with integrated illumination units. According to the invention the illumination units implemented as LEDs, in the form of a linear array in the axial direction, are accommodated in a cylindrical hollow space which is located behind the picture sensor 14 arranged at the distal end 15 of the electronic endoscope, within an enveloping tube 28 enveloping the endoscope. Directly at the distal end of the electronic endoscope there are located, as is usual, the objective 13 and there behind the picture sensor 14 including the associated correction and infrared or blocking filter.

Electrical connection cables 19 run below the linear array of the LEDs 17 up to a plug connecter 18 attached at the proximal end of the endoscope 11. The LEDs 17 are supplied with voltage by the voltage supply lead 19 which goes to the CCD sensor 14, so that no additional leads are required, which means that apart from the cable 8 no additional cable is required for the voltage supply of the LEDs 17. The endoscope 11 shown in FIG. 2 may be connected to the presently commercially available camera controller 4 (FIG. 1).

The illumination light goes from the individual LEDs 17 via the individual fiber-optic bundles 16 to the distal end 15 of the electronic endoscope 11.

The individual fiber-optic bundles 16 are with this grouped together to a distal fiber-optic bundle which at the distal end 15 of the endoscope 11 encloses the objective e.g. circularly or half-moon shaped. Seen from the outer appearance, the endoscope shown in FIG. 2 differs only from a conventional electronic endoscope by way of the omission of the connection socket which, with the conventional endoscope, is required for connecting the outer fiber-optic.

Figure 3A:
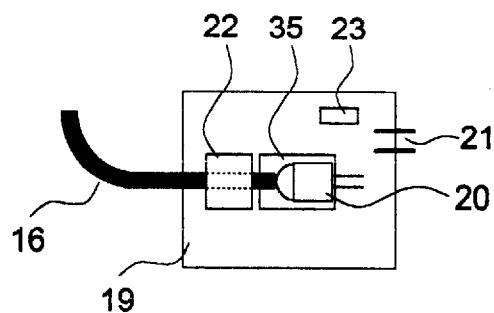

In FIG. 3a there is shown a first embodiment form of an illumination unit according to FIG. 2. On a circuit board 19 which has a rectangular relief 35 there are accommodated all components of the illumination unit. The rectangular relief 35 serves the assembly of white LEDs 20. Here with this embodiment form it is the case of an LED in a standard housing, which for example has an outer diameter of approximately 3 mm. This white LED 20 with its connection pins is electrically directly connected to the circuit board 19, e.g. soldered on, and is supplied with voltage via two connection leads 21. The operating current of the white LED 20 is determined with the help of a prior resistance, a constant current source or a pulse duration modulator 23.

The fiber-optic bundle 16 allocated to the LED 20 is with the help of a mounting 22 mounted on the circuit board 19 and is fixed in a manner such that there results an optimal position between the entry surface of the fiber-optic 16 and of the LED 20. The white light emitted by the LED may thus with low losses be coupled into the fiber-optic 16 and led to the distal end of the electronic endoscope 11.

Figure 3B:
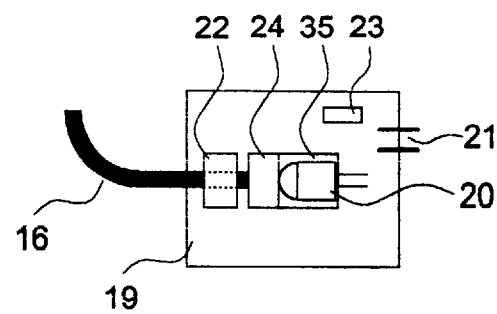

FIG. 3b shows a second embodiment form of a illumination unit 17 integrating an LED 20. Principally the embodiment form corresponds to that shown in FIG. 3a. The difference lies in the fact that between the fiber-optic 16 and LED 20 emitting white light there is located an optical system 24. This may then be advantageous when according to the irradiation characteristics and diameter of the LED 20 emitting white light, the emitted light may not be coupled into the fiber optic 16 directly and with low losses.

Figure 3C:
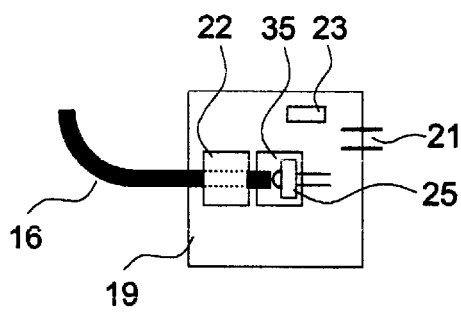

In FIG. 3c there is shown a further embodiment form of an illumination unit 17 containing an LED 25. Principally with this it is the case of the same embodiment as in FIG. 3a. As a LED 25 emitting white light here however an LED in a SMD housing (Surface Mount Device) is applied, since this constructional form is better suited to this application on account of the lower external dimensions.

Figure 3D:
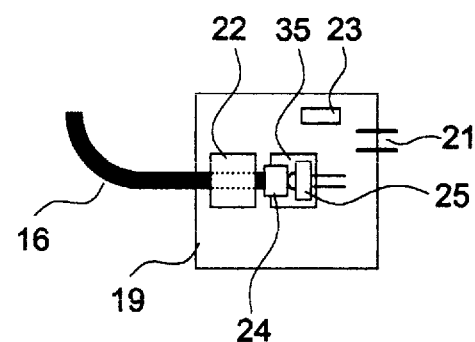

FIG. 3d shows a fourth embodiment form of the illumination unit 17 which is equipped with a SMD-LED 25 emitting white light. In contrast to the embodiment form shown in FIG. 3c this has an optical system 24 between the LED 25 and the LED-side end of the fiber optic 16. This optical system 24 as with the embodiment form shown in FIG. 3b serves the low-loss optimization of the coupling of light into the fiber-optic 16.

Figure 4B:
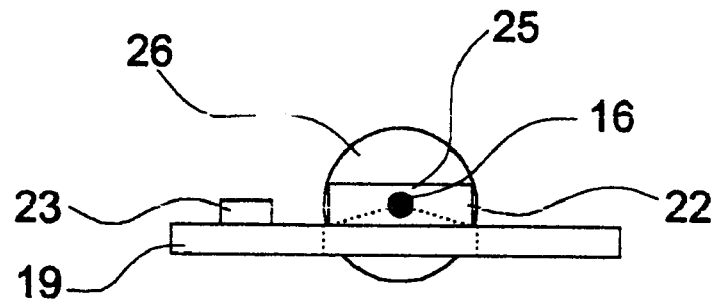
Figure 4A:
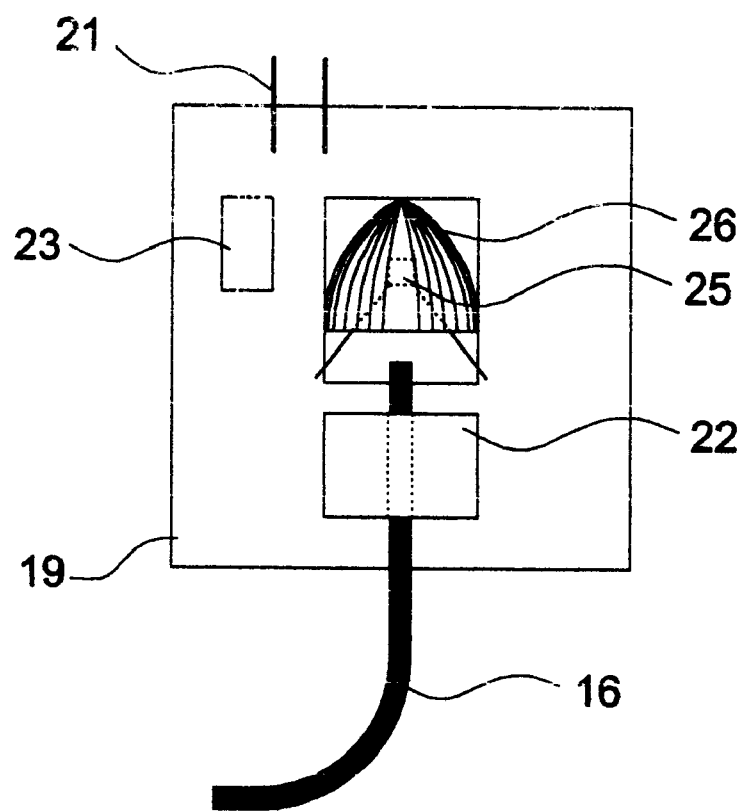

The FIGS. 4a and 4b show in each case in a plan view and from the side an LED 25 in the illumination unit which differs from the principle construction of the FIGS. 3a–3d in that the white light emitted by the LED 25 is not directly coupled into the fiber-optic 16, but firstly is reflected at a reflector 26. Such an arrangement forms a miniature mirror lamp with a white LED as a burner. The reflector 26 has preferably an elliptical cross section. Such a reflector 26 has two focal points of which one lies within the reflector and the other outside the reflector. In the focal point within the reflector there is placed a SMD-LED 25. With this as also in the FIGS. 3c and 3d it is the case of a SMD-LED since only it has the large irradiation angle of typically 160° necessary for such an arrangement.

The fiber-optic 16 is positioned with the mounting 33 such that the light entry surface in the second focal point is located outside the reflector 26. Thus the light emitted by the LED 25 and reflected at the reflector 26 is optimally coupled into the fiber-optic 16 without a coupling optic 24 being required as with the embodiment types shown in the FIGS. 3b and 3d.

Figure 5B:
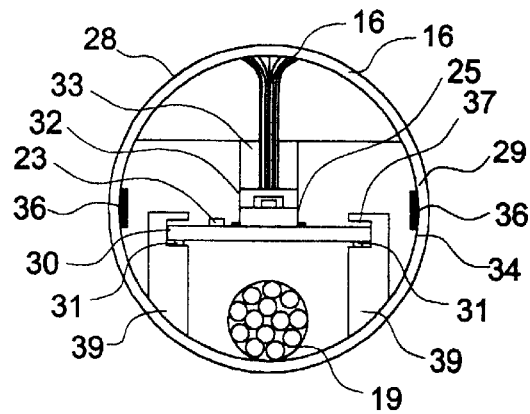
Figure 5A:
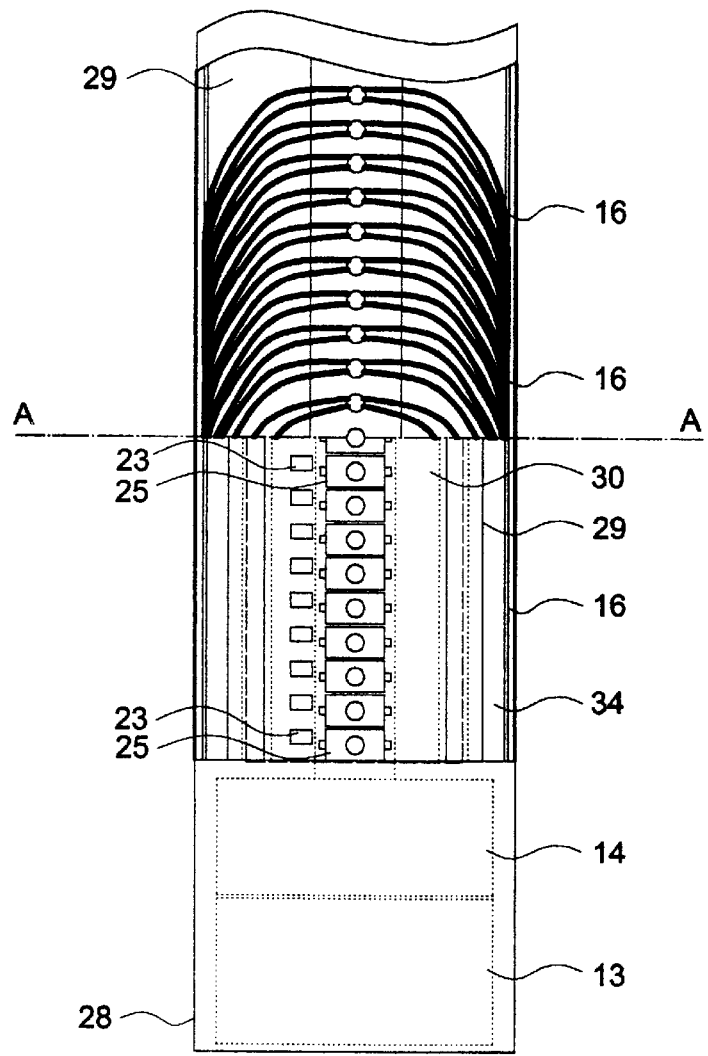

The FIGS. 5a and 5b show an embodiment, optimized from the point of view of manufacturing technology, of an electronic endoscope with illumination units represented in FIGS. 3c and 3d. With this characterizing is the fact that the LEDs 25 emitting white light are all accommodated on a common circuit board and that it is the case of a modular construction type. By way of this a cost-optimized and function-optimized construction is achieved.

The array of LEDs arranged on the common circuit board 30 linearly in the axial direction is located, as already mentioned by way of FIG. 2, within an outer enveloping tube 28 of the endoscope. Within the outer enveloping tube 28 there is located a partly divided, upper inner enveloping tube 29 and a lower inner enveloping tube 34. Between the outer enveloping tube 28 and the inner enveloping tubes 29, 34 the fiber-optics 16 are led from each white LED 25 to the distal end of the endoscope. At this end as already mentioned there are arranged the objective 13 and the picture sensor 14 (FIG. 2). Connection leads 19 which lead from the picture sensor 14 to the proximally arranged plug 18 (FIG. 2) run below the circuit board 30.

The circuit board 30 begins directly after the picture sensor 14. All electronic components of the illumination units, i.e. the LEDs and where appropriate the electronic circuit or the prior resistance 23 are assembled on the circuit board 30. From its distal end up to the distal beginning of the circuit board 30 the inner enveloping tube is formed as one piece. Thereafter the inner enveloping tube is designed in two parts as a lower inner enveloping tube 34 and an upper inner enveloping tube 29. From this location, on the lower inner enveloping tube 34 there are assembled all components which are required for mounting the circuit board. In the upper inner enveloping tube 29 there are assembled the components which are required for mounting the fiber-optics or fiber-optic fiber bundle 16 and for coupling the light emitted by the white LEDs 25. It must be noted at this location that in FIG. 5a after the picture sensor 14 up to the section plane A—A the electronic endoscope is shown with a cut-out upper inner enveloping tube 29, and from the section plane A—A, with an assembled upper inner enveloping tube 29, however without the outer enveloping tube 28.

By way of the cross section shown in FIG. 5b, in the section plane A—A now the construction is described in more detail. At the base of the inner lower enveloping tube 34 there is located the connection cable 19 to the picture sensor 14. On the lower inner enveloping tube 34 there is assembled a mounting 39 for accommodating the circuit board 30. In this mounting 39 there are located two grooves 37, in which the circuit board 30 is held. The circuit board thickness is with this less than the width of the groove 37. In both grooves 37 on the other side there are assembled spring members 31 which lift the circuit board 30 in the direction of the upper part of the grooves 37. The circuit board 30 is thus resiliently mounted.

On the circuit board 30 are accommodated the LEDs 25 with the associated prior resistances or the electronic circuit 23. The supply voltage reaches the circuit board 30 via contacts with the spring members 31 assembled in the grooves 31. The upper inner enveloping tube 29 contains mountings 33 for all fiber-optics contained in the electronic endoscope and the possible present optical systems directly mounted thereon, including the mounting 32 for the optimized coupling of the light emitted by the LEDs into the fiber-optics 16.

If LEDs are applied which are suitable for the direct coupling into the fiber-optics the optical systems may be done away with. The fiber-optics which exit at the upper side of the inner enveloping tube 29 are uniformly distributed on the circumference between the outer and inner enveloping tube so that at the distal end of the endoscope there is ensured a uniform light distribution. The upper inner enveloping tube 29 with latching mechanisms 36 which are located at the side wall of the two inner enveloping tube halves, is connected to the lower enveloping tube 34.

The assembly of the endoscope is effected as follows. All electronic components are assembled in or on the lower inner enveloping tube. The circuit board 30 from the proximal end is pushed in the distal direction into the grooves 37 in the mounting 39 up to the end position. The spring members 31 acting as contacts with this press the circuit board on the upper part of the grooves 37 and simultaneously create the electrical contact of the circuit board to the supply voltage. The upper inner enveloping tube 29 preassembled with the fiber-optic bundles 16 is now placed onto the circuit board and with a short pressure in the direction of the circuit board 30 is latched onto the lower inner enveloping tube. With this the mounting 33 of the fiber optic bundle 16 or the mounting 32 of the optical system press the circuit board slightly downwards so that there results a simply assemblable and again releasable connection between the mechanics, fiber-optic bundles and the electronics. Furthermore before the final putting together, the electronic part and the optical-mechanical part may be individually checked.

Figure 6A:
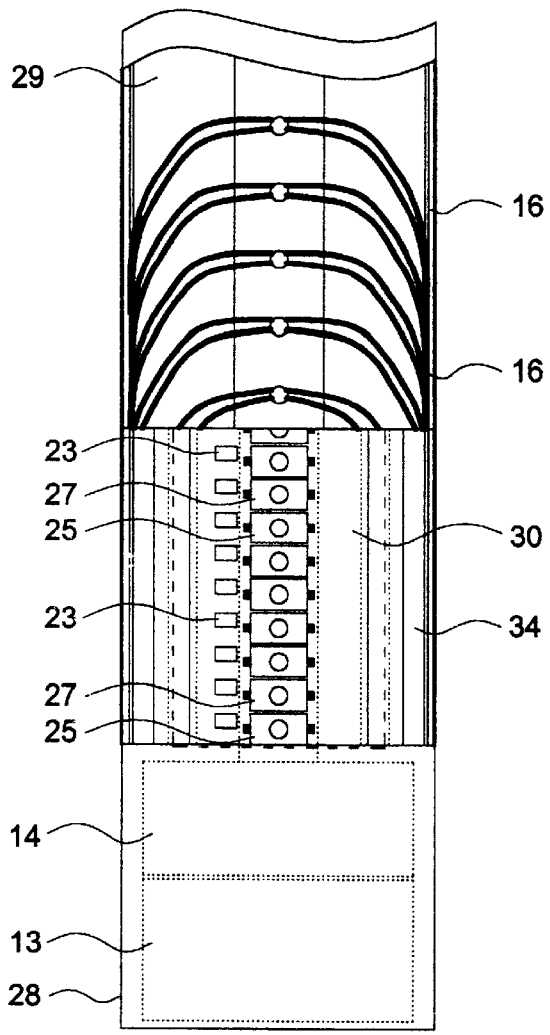
Figure 6B:
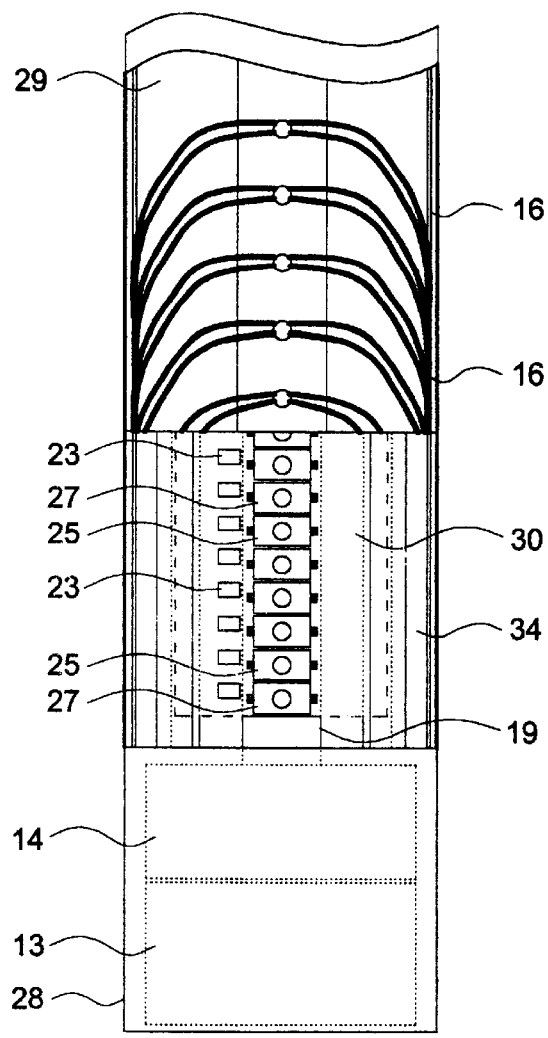

In the FIGS. 6a and 6b there is shown an advantageous further formation of the above described arrangement, shown in FIGS. 5a and 5b, of an electronic endoscope according to the invention which may be realized specially with the if construction shown in FIGS. 5a and 5b. The basic concept with this is to alternate the white LEDS arranged commonly on the circuit board 30 according to FIGS. 5a and 5b, with LEDs 27 which emit light with a certain wavelength. Here it is to be mentioned that LEDs emitting white light in contrast to LEDs emitting colored light have a continuous spectrum. The basis of an LED emitting white light is an LED emitting blue light which stimulates a phosphor material which in turn emits light of a certain wavelength region. The additive mixture of the two light types results in a white light with a continuous spectrum. For illumination purposes light with a continuous spectrum is required, since an object only reflects light in the case that its reflection wavelength is contained in the illumination light.

On the other hand for other applications, e.g. photodynamic diagnosis (PDD) monochromatic light, i.e. light of a very definite wavelength is required which stimulates a coloring for example accumulating in cancerous tissue to emit light of another wavelength (fluorescence light). With this diagnosis method it may be ascertained whether it is the case of healthy tissue or cancerous tissue. In the state of the art with the help of a light source comprising a short-arc lamp by way of a filter the illumination light is filtered into a narrow frequency band. Furthermore special fiber-optics are applied, and in the endoscope likewise filters are yet required for improved color differentiation.

With the arrangements shown in FIGS. 6a and 6b it is now possible to produce white light for the general illumination as this is already possible with the electronic endoscope shown in FIGS. 5a and 5b, and additionally to produce monochromatic light for such special, above described diagnosis methods. This is achieved by the alternating arrangement of white LEDs 25 and LEDs 27 emitting monochromatic light. For changing over between white illumination light and monochromatic diagnosis light the fiber-optics 16 are arranged in the upper inner enveloping tube 29 such that in comparison to the arrangement shown in the FIGS. 5a and 5b, always one fiber-optic is left out so that only every second LED can be coupled to a fiber-optic 16.

The circuit board 30 is displaceable in the axial direction. If now the circuit board 30 by way of an actuator, e.g. a piezoelectric actuator is displaced proximally by the distance of an LED, which is possible without further ado on account of the resilient mounting effected by the spring member 31, then under the fiber-optics are now the LEDs 27 which emit a certain wavelength, e.g. blue light. Thus the electronic endoscope shown in FIGS. 6a and 6b may be changed over between two illumination types. With this it is to be emphasized that with the two illumination types always all the fiber-optics 16 integrated into the electronic endoscope may be used, that thus always a maximum of illumination light is available independent of the chosen operating type.

An alternative embodiment form of an electronic endoscope not shown in the figures may comprise, arranged in groups, LEDs which emit white light and LEDs which emit monochromatic light. If light coming from these LEDs is simultaneously coupled into the fiber-optic the illumination light which exits at the distal end of the endoscope may be corrected with regard to the color temperature of the white light.

A further alternative may effect a change-over between a first color temperature and a second color temperature of the illumination light by way a change-over between a first group containing n white LEDs and m monochromatic LEDs and a second LED group containing i white LEDs and k monochromatic LEDs. Such a change-over may in particular be achieved by a useful distribution of LEDs assembled together on a circuit board according to FIGS. 5a and 5b or 6a and 6b and an axial displacement of the circuit board 30 as explained above by way of FIGS. 6a and 6b.

What is claimed is:

1. An electronic endoscope with a picture sensor located at its distal end and with several illumination units (LEDs) integrated in the endoscope, for producing illumination light irradiated at the distal endoscope end, wherein the illumination units are arranged as a linear and axial array of LEDs in a space, of an enveloping tube, connecting proximally to the picture sensor, wherein to the LEDs there are allocated fiber-optics into which the light irradiated by the LEDs may be coupled and wherein the fiber-optics run up to the distal endoscope end and here are grouped together to a bundle.

2. An endoscope according to claim 1, characterized in that the LEDs emit white light.

3. An endoscope according to claim 1, wherein the LEDs emit white and monochromatic light.

4. An endoscope according to claim 3, wherein the fiber-optic bundle at the distal end simultaneously emits white and monochromatic light for the spectral correction of the irradiated white light.

5. An endoscope according to claim 3, wherein there are provided means for the spectral change-over of the light irradiated from the fiber-optic bundle at the distal end.

6. An endoscope according to claim 5, wherein there are provided means for changing over the color temperature of the light.

7. An endoscope according to claim 6, wherein the change-over means are set up for changing over an LED group comprising n white LEDs and m monochromatic LEDs and a second group comprising i white LEDs and k monochromatic LEDs.

8. An endoscope according to claim 5, wherein the change-over means change over the LEDs.

9. An endoscope according to claim 1, wherein the array of LEDs contains a first group of LEDs irradiating white light and a second group of LEDs irradiating monochromatic light.

10. An endoscope according to claim 1, wherein between each LED and the associated fiber-optic there is arranged an optical system.

11. An endoscope according to claim 1, wherein the light produced by each LED after reflection at a reflector is coupled into the associated fiber-optic.

12. An endoscope according to claim 11, wherein the reflector is formed as a hollow mirror with an elliptical cross section.

13. An endoscope according to claim 1, wherein the array of all LEDs is arranged on a common circuit board such that the light irradiation of all LEDs lies radially in one direction.

14. An endoscope according to claim 13, wherein only fiber optics from every second LED are guided firstly radially outwards and then within an enveloping tube to the distal end.

15. An endoscope according to claim 14, wherein every even-numbered LED emits white light and every odd-numbered LED monochromatic light and wherein a change-over means for the axial displacement of the common circuit board is set up such that into the fiber-optic in a first position of the circuit board there is coupled only white light from the even-numbered LEDs and in a second position of the circuit board there is coupled only monochromatic light from the odd-numbered LEDs.

16. An endoscope according to claim 13, characterized in that the fiber-optics of each LED are guided firstly radially outwards and then within an enveloping tube to the distal end.

17. An endoscope according to claim 1, wherein the supply voltage for the LEDs is derived from the operating voltage of the picture sensor.

* * * * *